United States Patent [19]
deSolms et al.

[11] Patent Number: 5,468,733
[45] Date of Patent: Nov. 21, 1995

[54] INHIBITORS OF FARNESYL-PROTEIN TRANSFERASE

[75] Inventors: S. Jane deSolms, Norristown; Elizabeth A. Giuliani, Lansdale; Samuel L. Graham, Schwenksville, all of Pa.

[73] Assignee: Merck & Co., Inc., Rahway, N.J.

[21] Appl. No.: 130,032

[22] Filed: Sep. 30, 1993

[51] Int. Cl.$^6$ .................. A61K 38/00; C07D 207/12; C07D 207/24; C07D 211/40
[52] U.S. Cl. .............. 514/19; 548/550; 546/216
[58] Field of Search ................ 514/19; 548/550; 546/216

[56] References Cited

U.S. PATENT DOCUMENTS 5,238,922  8/1993  Graham et al. ................... 514/18

OTHER PUBLICATIONS

Kohl et al Proc. Natl. Acad. Sci., USA vol. 91 p. 9141 (1994).
Kohl, et al., Science, vol. 30, pp. 1934–1937 (1993).
James, et al., Science, vol. 30, pp. 1937–1942 (1993).
Omura, et al, Journal of Antibiotics, vol. 46, pp. 222–229 (1993).
Shiomi, et al., Jour. of Antibiotics, vol. 46, pp. 229–234 (1993).

*Primary Examiner*—Jill Warden
*Assistant Examiner*—Sheela J. Huff
*Attorney, Agent, or Firm*—David A. Muthard; Mark R. Daniel; Joseph F. DiPrima

[57] ABSTRACT

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

25 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbial. Rev.* 53:171–286(1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al, *Proc. Natl Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J* 8:1093–1098 (1989); Hancock et al., *Cell* 57:1167–1177 (1989); Ki-Ras lacks the palmitate acceptor Cys. The last 3 amino acids at the Ras C-terminal end are removed proteolytically, and methyl esterification occurs at the new C-terminus (Hancock et al, ibid). Fungal mating factor and mammalian nuclear lamins undergo identical modification steps (Anderegg et al, *J. Bid. Chem.* 263:18236 (1988); Farnsworth et al., *J. Biol, Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss al., Cell, 62:81–88 (1990); Schaber et al., *J. Biol Chem.*, 265:14701–14704 (1990); Schafer et al., Science, 249:1133–1139 (190); Manne et al., *Proc Natl. Acad. Sci USA*, 87: 7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box farnesylation signal domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1980)). Cytosol-localized forms of Ras with normal GTPase activity do not act as inhibitors. Gibbs et al., ibid, showed this effect in *Xenopus oocytes* and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Partial reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras Cys-Aaa$^1$-Aaa$^2$-Xaa (CAAX) box with a farnesyl group. While inhibition of farnesyl pyrophosphate biosynthesis by inhibiting HMG-CoA reductase blocks Ras membrane localization in vivo inhibits Ras function, inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue in a CAAX sequence inhibit Ras farnesylation (Schaber et al., ibid; Reiss et. al., ibid; Reiss et. al., *PNAS*, 88:732–736 (1991)). Such inhibitors may inhibit while serving as alternate substrates for the Ras farnesyl-transferase enzyme, or may be purely competitive inhibitors (U.S. Pat. No. 5,141,851, University of Texas).

Inhibitors of Ras farnesyl-protein transferase (FPTase) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. The exception to this generalization is a class of natural products known as the pepticinnamins (Omura, et al., *J. Antibiotics* 46:222 (1993). In general, deletion of the thiol from a CAAX derivative dramatically reduces the inhibitory potency of these compounds. However, the thiol group potentially places limitations on the therapeutic application of FPTase inhibitors with respect to pharmacokinetics, pharmacodynamics and toxicity. Therefore, a functional replacement for the thiol is desirable. With the exception of the pepticinnamins, non-thiol FPTase inhibitors that are competitive with the Ras substrate have not been described and are the subject of this invention.

It is, therefore, an object of this invention to develop tetrapeptide-based compounds which do not have a thiol moiety, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae:

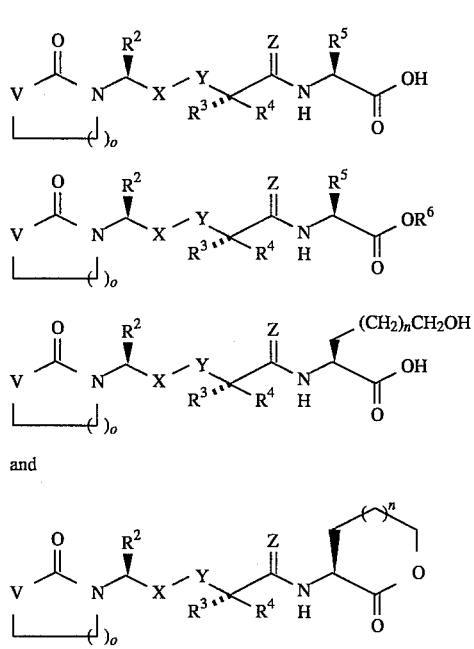

and

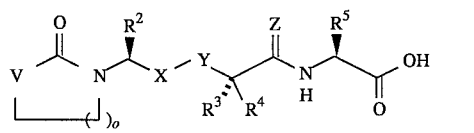

DETAILED DESCRIPTION OF THE INVENTION

The compounds of this invention inhibit the farnesylation of Ras. In a first embodiment of this invention, the Ras farnesyl transferase inhibitors are illustrated by the formula I:

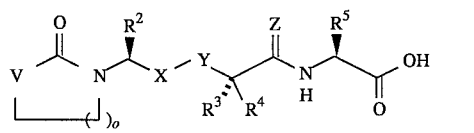

wherein:

V is $CH_2$, O, S, HN, or $R^7N$;

$R^2$, $R^3$, $R^4$ and $R^5$ are independently the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X-Y is

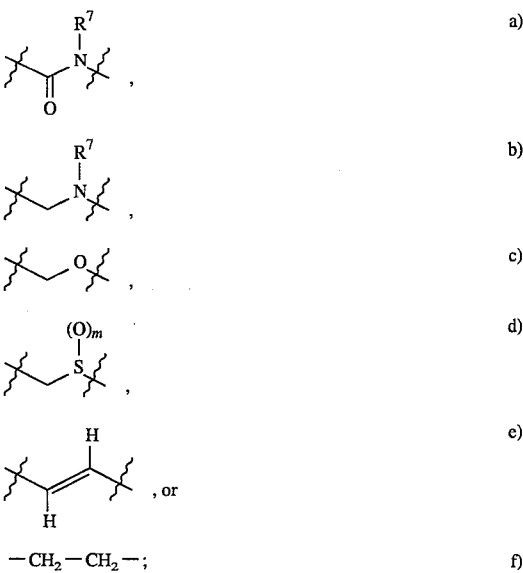

$R^7$ is an alkyl group, wherein the alkyl group comprises straight chain or branched chain hydrocarbons of 1 to 6 carbon atoms, which may be substituted with an aromatic or heteroaromatic group;

Z is $H_2$ or O;

m is 0, 1 or 2; and o is 0, 1, 2 or 3;

or the pharmaceutically acceptable salts thereof.

In a second embodiment of this invention the prodrugs of compounds of formula I are illustrated by the formula II:

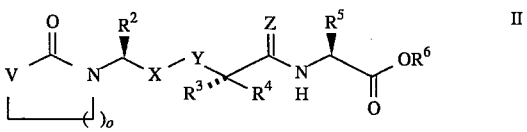

wherein $CH_2$, O, S, HN, or $R^7N$;

$R^2$, $R^3$, $R^4$ and $R^5$ are independently the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X-Y is

-continued

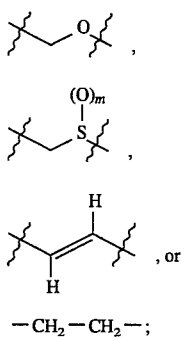

R⁶ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;

R⁷ is an alkyl group, wherein the alkyl group comprises straight chain or branched chain hydrocarbons of 1 to 6 carbon atoms, which may be substituted with an aromatic or heteroaromatic group;

Z is $H_2$ or O; and m is 0, 1 or 2;

o is 0, 1, 2 or 3;

or the pharmaceutically acceptable salts.

In a third embodiment of this invention, the inhibitors of farnesyl transferase are illustrated by the formula III:

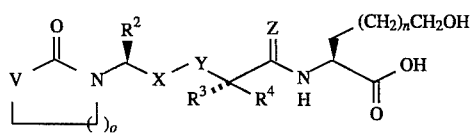

wherein:

V is $CH_2$, O, S, HN, or $R^7N$;

$R^2$, $R^3$ and $R^4$ are independently the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X-Y is

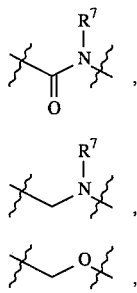

-continued

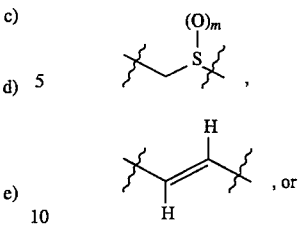

$-CH_2-CH_2-$;  f)

R⁷ is an alkyl group, wherein the alkyl group comprises straight chain or branched chain hydrocarbons of 1 to 6 carbon atoms, which may be substituted with an aromatic or heteroaromatic group;

Z is $H_2$ or O;

n is 0, 1 or 2;

m is 0, 1 or 2; and o is 0, 1, 2 or 3;

or the pharmaceutically acceptable salts thereof.

In a fourth embodiment of this invention the prodrugs of compounds of formula III are illustrated by the formula IV:

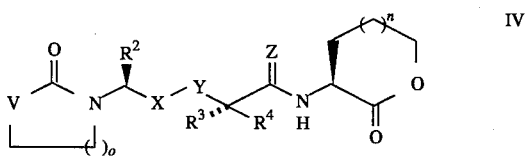

wherein:

V is $CH_2$, O, S, HN, or $R^7N$;

$R^2$, $R^3$ and $R^4$ are independently the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X-Y is

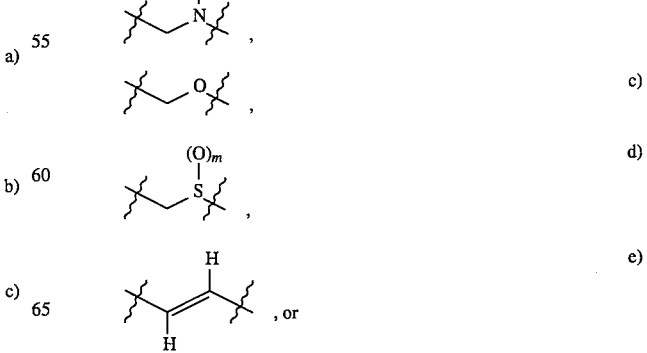

-continued $-CH_2-CH_2-;$        f)

$R^7$ is an alkyl group, wherein the alkyl group comprises straight chain or branched chain hydrocarbons of 1 to 6 carbon atoms, which may be substituted with an aromatic or heteroaromatic group;

Z is $H_2$ or O;

n is 0, 1 or 2;

m is 0, 1 or 2; and o is 0, 1, 2 or 3;

or the pharmaceutically acceptable salts thereof.

The preferred compounds of this invention are as follows:

N-[2(S)-(pyrrolidin-2-on-1-yl)-3-methylbutanoyl]-isoleucyl-methionine;

or

N-[2(S)-(piperidin-2-on-1-yl)-3-methylbutanoyl]-isoleucy-methionine; or the pharmaceutically acceptable salts thereof.

In the present invention, the amino acids which are disclosed are identified both by conventional 3 letter and single letter abbreviations as indicated below:

| Alanine | Ala | A |
|---|---|---|
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threoniune | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the examples that follow are:

| $Ac_2O$ | Acetic anhydride; |
|---|---|
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethylcarbodiimide hydrochloride; |
| HOBT | 1-Hydroxybenzotriazole hydrate; |
| $Et_3N$ | Triethylamine; |
| EtOAc | Ethyl acetate. |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |

-continued

| MsCl | Methanesulfonyl chloride; |
| NaHMDS | Sodium bis(trimethylsilyl)amide |
| Py | Pyridine; |
| TFA | Trifluoroacetic acid; |
| THF | Tetrahydrofuran; |

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

Reaction D. Peptide bond formation and protecting group cleavage using standard solution or solid phase methodologies.

Reaction E. Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes.

REACTION SCHEME A
Reaction A. Coupling of residues to form an amide bond

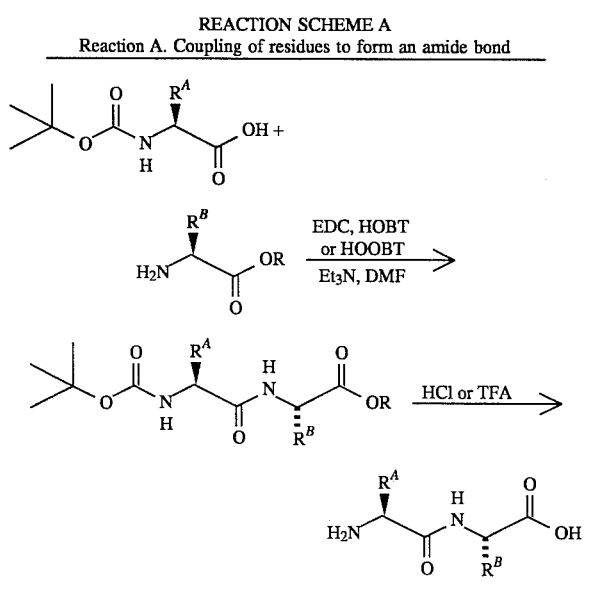

REACTION SCHEME B
Reaction B. Preparation of reduced peptide subunits by reductive alkylation

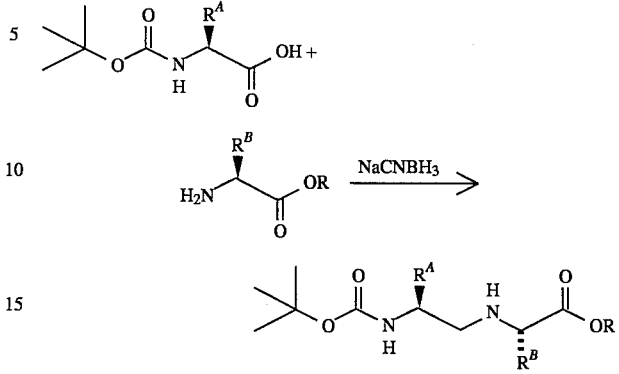

REACTION SCHEME C
Reaction C. Alkylation/reductive alkylation of reduced peptide subunits

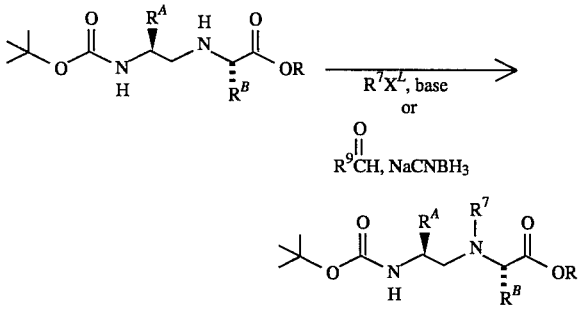

REACTION SCHEME D
Reaction D. Coupling of residues to form an amide bond

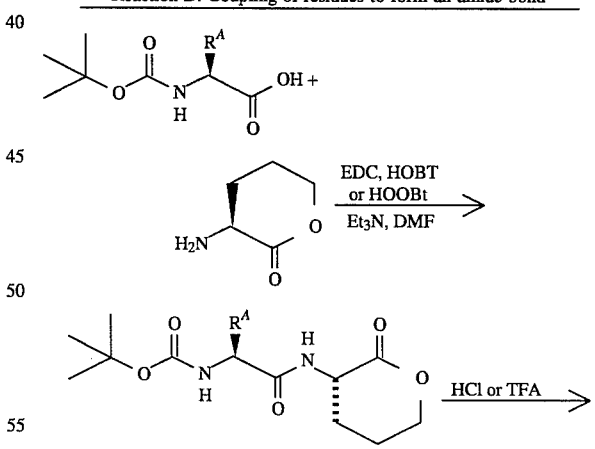

-continued
REACTION SCHEME D
Reaction D. Coupling of residues to form an amide bond

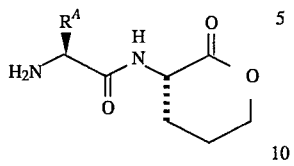

REACTION SCHEME E
Reaction E. Preparation of reduced dipeptides from peptides

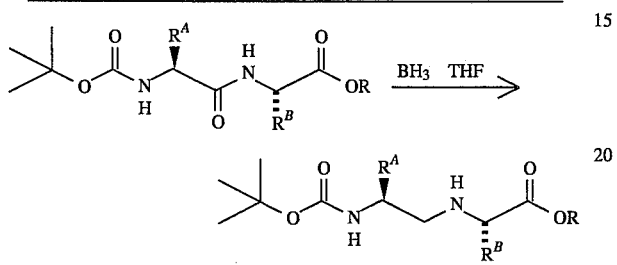

where $R^A$ and $R^B$ are $R^2$, $R^3$ or $R^4$ as previously defined; $X^L$ is a leaving group, e.g., $Br^-$, $I^-$ or $MsO^-$; and $R^8$ is defined such that $R^7$ is generated by the reductive alkylation process.

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme F, Step B, Part 1), and stereospecific boron triflouride or zinc chloride activated organo-magnesio, organo-lithio, or organo-zinc copper(1) cyanide $S_N2'$ displacement reaction (Scheme F, Step G). Through the use of optically pure N-Boc amino acids as starting material and these two key reactions, the stereochemistry of the final products is well defined. In Step H of Scheme F, the lactam ring is incorporated by acylation of the primary amino group with 4-chlorobutyryl chloride and base-catalyzed cyclization.

The alkane analogs are prepared in a similar manner by including an additional catalytic hydrogenation step as outlined in Reaction Scheme G.

REACTION SCHEME F

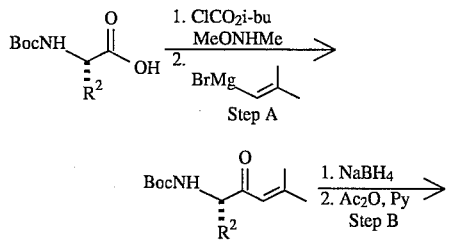

-continued
REACTION SCHEME F

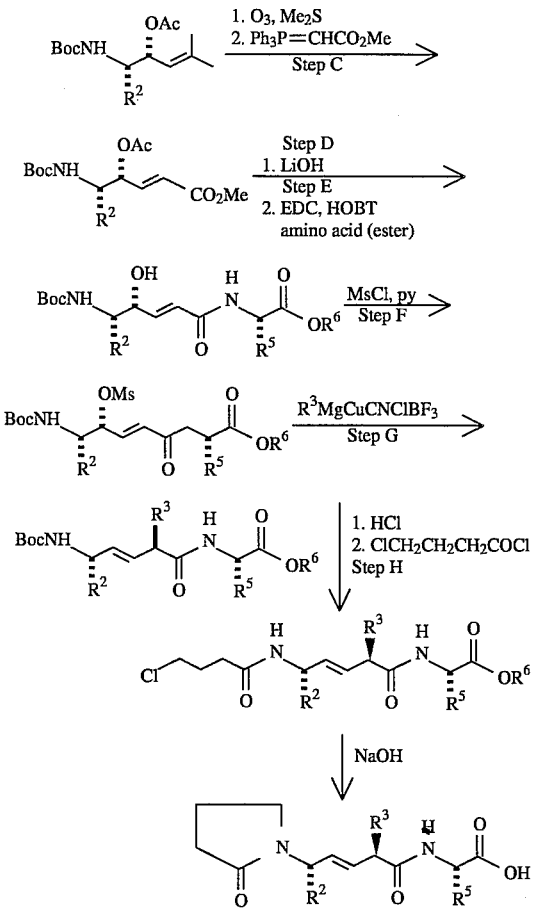

REACTION SCHEME G

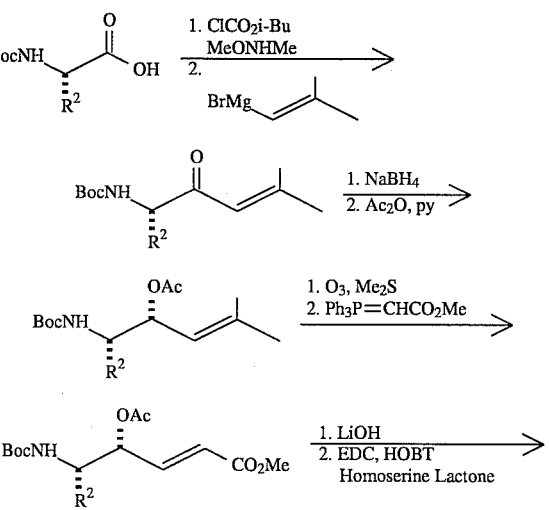

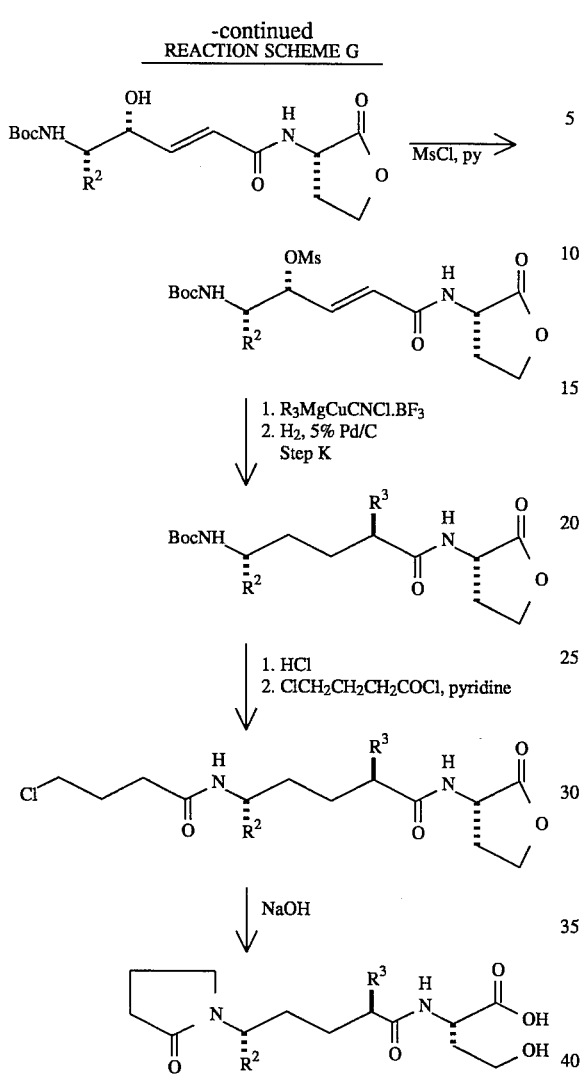

-continued
REACTION SCHEME G

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. The N-Boc derivative 4 is then obtained by the treatment of 3 with BOC anhydride and DMAP (4-dimethylaminopyridine) in methylene chloride. Alkylation of 4 with $R^3X^L$, where $X^L$ is a leaving group such as Br-, I- or Cl- in THF/DME (1,2-dimethoxyethane) in the presence of a suitable base, preferably NaHMDS [sodium bis(trimethylsilyl)amide], affords 5, which is retreated with NaHMDS followed by either protonation or the addition of an alkyl halide $R^4X$ to give 6a or 6b, respectively. Alternatively, 6a can be prepared from 4 via an aldol condensation approach. Namely, deprotonation of 4 with NaHMDS followed by the addition of a carbonyl compound $R^7R^8CO$ gives the adduct 7. Dehydration of 7 can be effected by mesylation and subsequent elimination catalyzed by DBU (1,8-diazabicyclo[5.4.0]undec-7-ene) or the direct treatment of 7 with phosphorus oxychloride in pyridine to give olefin 8. Then, catalytic hydrogenation of 8 yields 6a. Direct hydrolysis of 6 with lithium hydrogen peroxide in aqueous THF will produce acid 9b. Sometimes, it is more efficient to carry out this conversion via a 2-step sequence, namely, hydrolysis of 6 in hydrochloric acid to afford 9a, which is then derivatized with BOC-ON or BOC anhydride to give 9b. The peptide coupling of acid 9b with either an alpha-aminolactone (e.g., homoserine lactone, etc.) or the ester of an amino acid is carried out under the conditions exemplified in the previously described references to yield derivative 10. Treatment of 10 with gaseous hydrogen chloride gives 11, which undergoes acylation with 4-chlorobutyryl chloride. Base treatment leads to lactam formation.

SCHEME H

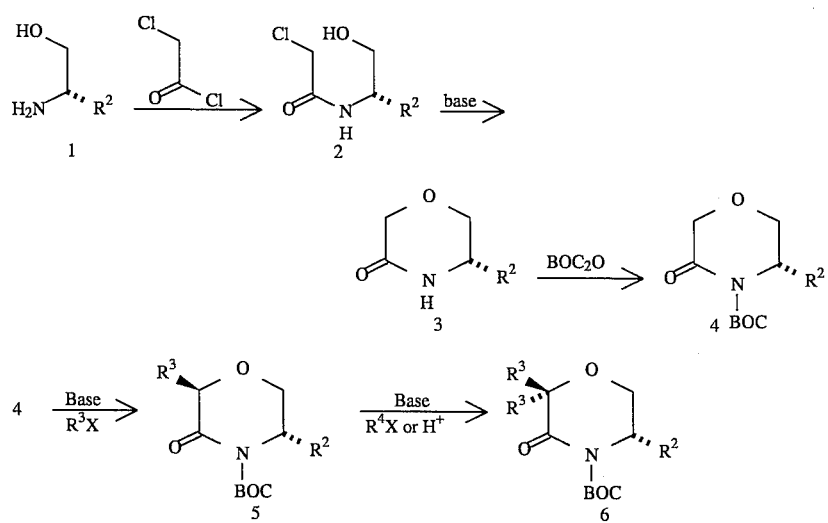

-continued
SCHEME H

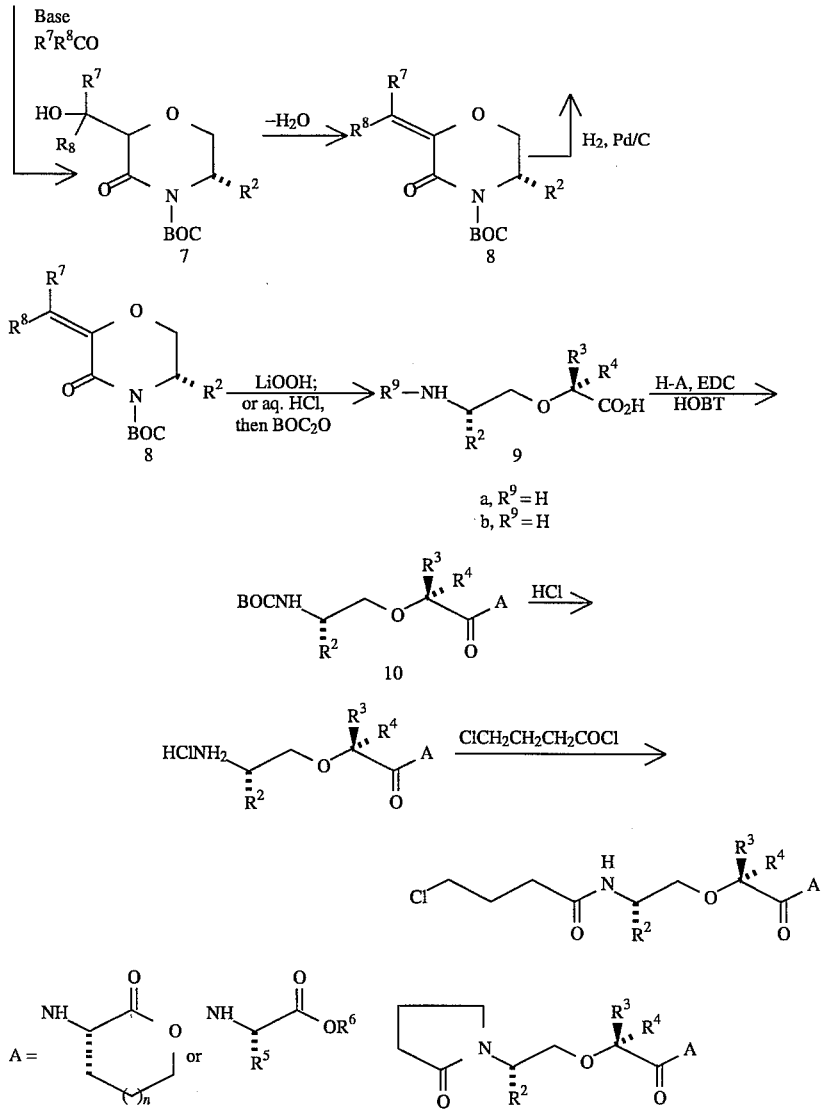

The thia, oxothia and dioxothia isostere compounds of this invention are prepared in accordance to the route depicted in Scheme I. Aminoalcohol 1 is derivatized with $BOC_2O$ to give 15. Mesylation of 15 followed by reaction with methyl a-mercaptoacetate in the presence of cesium carbonate gives sulfide 16. Removal of the BOC group in 16 with TFA followed by neutralization with di-isopropylethylamine leads to lactam 17. N-BOC derivative 18 is obtained via the reaction of 17 with BOC anhydride in THF catalyzed by DMAP. Sequential alkylation of 18 with the alkyl halides $R^3X$ and $R^4X$ in THF/DME using NaHDMS as the deprotonation reagent produces 19. Hydrolysis of 19 in hydrochloride to yield 20a, which is derivatized with Boc anhydride to yield 20b. The coupling of 20b with an alpha-aminolactone (e.g., homoserine lactone, etc.) or the ester of an amino acid is carried out under conventional conditions as exemplified in the previously described references to afford 21. Sulfide 21 is readily oxidized to sulfone 22 by the use of MCPBA (m-chloroperoxybenzoic acid). The N-BOC group of either 21 or 22 is readily removed by treatment with gaseous hydrogen chloride. The resultant amine hydrochloride 23 can be converted to the lactam as described above.

SCHEME I
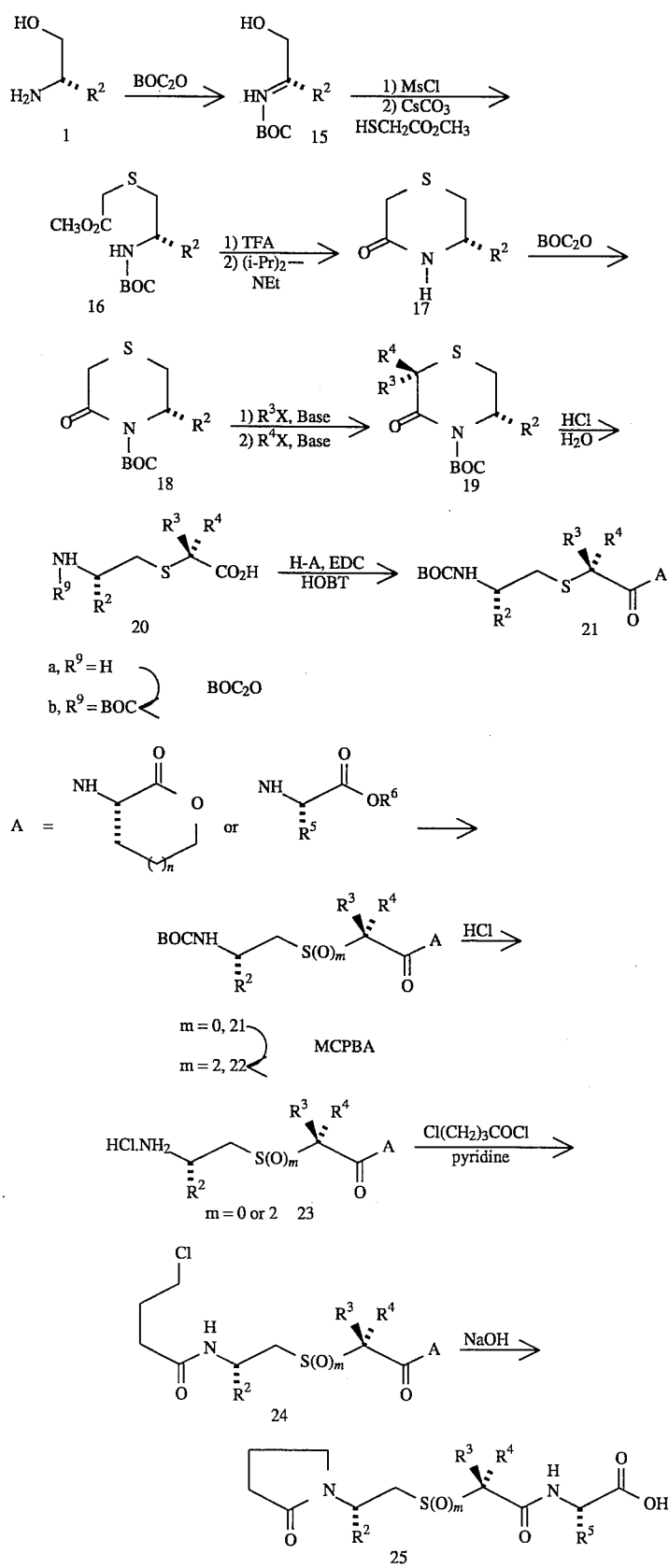

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

EXAMPLE 1

Preparation of
N-[2(S)-(pyrrolidin-2-on-1-yl)-3-methylbutanoyl]-isoleucyl-methionine Step A: Preparation of
N-4-chlorobutanoylvalyl-isoleucyl-methionine
methyl ester The hydrochloride salt of valyl-isoleucyl-methionine methyl ester was obtained using standard solution phase synthesis methods. To a suspension of this tripeptide (150 mg, 0.38 mmol) in 10 mL methylene chloride at 0° C. was added pyridine (61 mL, 0.75 mmol), 43 mL of 4-chlorobutanoyl chloride (0.38 mmol) and 5 drops of DMF. The mixture was stirred for 15 min. at 0° C. and then at room temperature overnight. The reaction was worked up in the standard manner to afford 130 mg of crude product. This material was further purified by chromatography on silica gel (98:2 methylene chloride:methanol) and trituration with a mixture of ether and methylene chloride. The solid product weighed 70 mg.

Step B: Preparation of
N-[2(S)-(pyrrolidin-2-on-1-yl)-3-methylbutanoyl]-isoleucyl-methionine The product of Step A was suspended in 5 mL of methanol and 0.6 mL of 1N NaOH was added. After 1 h. the methanol was evaporated, the residue was dissolved in water and filtered. The filtrate was acidified and the product was extracted into ethyl acetate. After standard workup, a solid was obtained, which was washed with water and ether. After drying the solid weighed 25 mg. FAB mass spectrum m/z=430 (M+1).

Anal. Calcd for $C_{20}H_{35}N_3O_5S.0.2H_2O$: C, 55.46; H, 8.24; N, 9.70. Found: C, 55.45; H, 7.88; N, 9.61.

EXAMPLE 2

Preparation of
N-[2(S)-(piperidin-2-on-1-yl)-3-methylbutanoyl]-isoleucyl-methionine Step A: Preparation of N-(5-chloropentanoyl)valine
methyl ester Using the method of Example 1, Step A, valine methyl ester and 5-chloropentanoyl chloride were coupled to provide N-(5-chloropentanoyl)valine methyl ester.

Step B: Preparation of Methyl
2(S)-(piperidin-2-on-1-yl)-3-methylbutanoate

A solution of 105 mg (0.42 mmol) of the product of Step A in 10 mL of dry THF was treated with 17 mg (0.43 mmol) of 60% NaH in oil dispersion at 0° C. for 1 h. TLC analysis indicated starting material was present and 2 mL of DMF was added. After 1.5 h. at 0° C., the solvent was evaporated and the mixture was worked up in the standard to give 90 mg of product.

Step C: Preparation of
2(S)-(Piperidin-2-on-1-yl)-3-methylbutanoic acid

The product of Step B was dissolved in 4 mL of methanol and 0.85 mL of 1N NaOH was added. The mixture was stirred overnight and the solvent was evaporated. The residue was dissolved in water, filtered and acidified. Ethyl acetate extraction and standard workup gave 30 mg of the title compound.

Step D: Preparation of
N-[2(S)-(piperidin-2-on-1-yl)-3-methylbutanoyl]-isoleucyl-methionine The product of Step C was coupled to the dipeptide isoleucyl-methionine methyl ester using a standard protocol. Following saponification of the methionine ester, the title compound was obtained. $^1$H-NMR of this material indicated that it was a 1:1 mixture of diastereomers, due to racemization of the valine residue.

EXAMPLE 3

In Vitro inhibition of Ras farnesyl transferase

Farnesyl-protein transferase (FTase) from bovine brain was chromatographed on DEAE-Sephacel-(Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS at 3.5 mM, 0.25 mM [$^3$H]FPP, and the indicated compounds were incubated with either a partially purified bovine enzyme preparation or a recombinant human enzyme preparation. The FTase data presented below in Table 1 reflects the ability of the test compound to inhibit RAS farnesylation in vitro, as described in Pompliano, et al., Biochemistry 31, 3800 (1992).

TABLE 1

| Inhibition of RAS farnesylation by compounds of this invention* | |
|---|---|
| | IC$_{50}$ |
| N-[2(S)-(pyrrolidin-2-on-1-yl)-3-methylbutanoyl]-isoleucyl-methionine | 2000 |
| N-[2(S)-(piperidin-2-on-1-yl)-3-methylbutanoyl]-isoleucyl-methionine | 6200 |

*(IC$_{50}$ is the concentration of the test compound which gives 50% inhibition of FTase under the described assay conditions).

What is claimed is:

1. A compound which inhibits Ras farnesyl-transferase having the formula I:

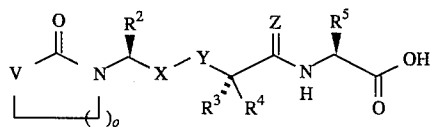

wherein:

V is CH$_2$;

R$^2$, R$^3$, R$^4$ and R$^5$ are independently the side chains of naturally occurring amino acids, including their oxidized forms which may be methionine sulfoxide or methionine sulfone, or in the alternative may be substituted or unsubstituted aliphatic or aromatic groups, such as allyl, cyclohexyl, phenyl or saturated chains of 2 to 8 carbon atoms which may be branched or unbranched, wherein the aliphatic substituents may be substituted with an aromatic ring;

X-Y is

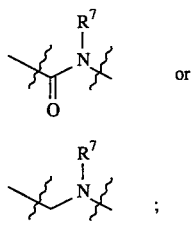

R$^7$ is an alkyl group, wherein the alkyl group comprises straight chain or branched chain hydrocarbons of 1 to 6 carbon atoms, which may be substituted with an aromatic group;

Z is H$_2$ or O;

m is 0, 1 or 2; and o is 0, 1, 2 or 3;

or the pharmaceutically acceptable salt thereof.

2. A prodrug of a compound of claim 1 having the formula II:

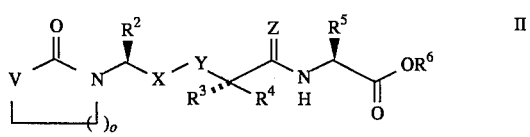

wherein:

V is CH$_2$;

R$^2$, R$^3$, R$^4$ and R$^5$ are independently the side chains of naturally occurring amino acids, including their oxidized forms which may be methionine sulfoxide or methionine sulfone, or in the alternative may be substituted or unsubstituted aliphatic or aromatic groups, such as allyl, cyclohexyl, phenyl or saturated chains or 2 to 8 carbon atoms which may be branched or unbranched, wherein the aliphatic substituents may be substituted with an aromatic ring;

X-Y is

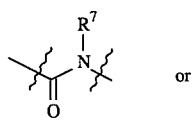

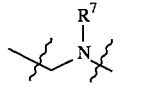

R$^6$ is a substituted or unsubstituted aliphatic, aromatic group such as saturated chains of 1 to 8 carbon atoms, which may be branched or unbranched, wherein the aliphatic substituent may be substituted with an aromatic ring;

R$^7$ is an alkyl group, wherein the alkyl group comprises straight chain or branched chain hydrocarbons of 1 to 6 carbon atoms, which may be substituted with an aromatic group;

Z is H$_2$ or O;

m is 0, 1 or 2; and o is 0, 1, 2 or 3;

or the pharmaceutically acceptable salts thereof.

3. A compound which inhibits Ras farnesyl-transferase having the formula III:

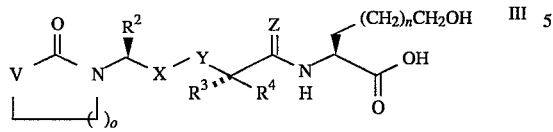

wherein:

V is CH$_2$;

R$^2$, R$^3$ and R$^4$ are independently the side chains of naturally occurring amino acids, including their oxidized forms which may be methionine sulfoxide or methionine sulfone, or in the alternative may be substituted or unsubstituted aliphatic or aromatic groups, such as allyl, cyclohexyl, phenyl or saturated chains of 2 to 8 carbon atoms which may be branched or unbranched, wherein the aliphatic substituents may be substituted with an aromatic ring;

X-Y is

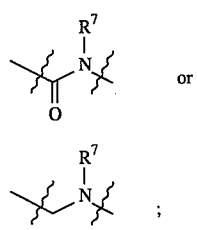

R$^7$ is an alkyl group, wherein the alkyl group comprises straight chain or branched chain hydrocarbons of 1 to 6 carbon atoms, which may be substituted with an aromatic group;

Z is H$_2$ or O;

n is 0, 1 or 2;

m is 0, 1 or 2; and o is 0, 1, 2 or 3;

or the pharmaceutically acceptable salts thereof.

4. A prodrug of a compound of claim 3 of the formula IV:

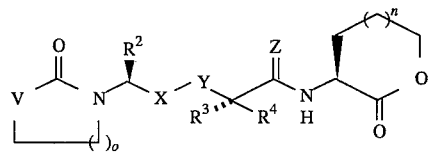

wherein:

V is CH$_2$;

R$^2$, R$^3$ and R$^4$ are independently the side chains of naturally occurring amino acids, including their oxidized forms which may be methionine sulfoxide or methionine sulfone, or in the alternative may be substituted or unsubstituted aliphatic or aromatic groups, such as allyl, cyclohexyl, phenyl or saturated chains of 2 to 8 carbon atoms which may be branched or unbranched, wherein the aliphatic substituents may be substituted with an aromatic ring;

X-Y is

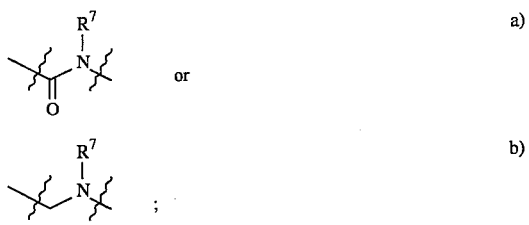

R$^7$ is an alkyl group, wherein the alkyl group comprises straight chain or branched chain hydrocarbons of 1 to 6 carbon atoms, which may be substituted with an aromatic group;

Z is H$_2$ or O;

n is 0, 1 or 2;

m is 0, 1 or 2; and o is 0, 1, 2 or 3 or the pharmaceutically acceptable salts thereof.

5. A compound of claim 1 which inhibits farnesyl-protein transferase which is:

N-[2(S)-(pyrrolidin-2-on-1-yl)-3-methylbutanoyl]-isoleucyl-methionine; or

N-[2(S)-(piperidin-2-on-1-yl)-3-methylbutanoyl]-isoleucyl-methionine; or the pharmaceutically acceptable salts thereof.

6. A compound which inhibits farnesyl-protein transferase which is:

N-[2(S)-(pyrrolidin-2-on-1-yl )-3-methylbutanoyl]-isoleucyl-methionine or the pharmaceutically acceptable salts thereof.

7. A compound which inhibits farnesyl-protein transferase which is:

N-([2(S)-(piperidin-2-on-1-yl)-3-methylbutanoyl]-isoleucyl-methionine or the pharmaceutically acceptable salt thereof.

8. A pharmaceutical composition comprising a pharmaceutical carrier, and dispersed therein, a therapeutically effective amount of a compound of claim 1.

9. A pharmaceutical composition comprising a pharmaceutical carrier, and dispersed therein, a therapeutically effective amount of a compound of claim 2.

10. A pharmaceutical composition comprising a pharmaceutical carder, and dispersed therein, a therapeutically effective amount of a compound of claim 3.

11. A pharmaceutical composition comprising a pharmaceutical carrier, and dispersed therein, a therapeutically effective amount of a compound of claim 4.

12. A pharmaceutical composition comprising a pharmaceutical carrier, and dispersed therein, a therapeutically effective amount of a compound of claim 6.

13. A pharmaceutical composition comprising or a pharmaceutical carder, and dispersed therein, a therapeutically effective amount of a composition of claim 7.

14. A method for inhibiting farnesylation of Ras protein in said mammal which comprises administering to a mammal in need thereof a therapeutically effective amount of a composition of claim 8.

15. A method for inhibiting farnesylation of Ras protein in said mammal which comprises administering to a mammal in need thereof a therapeutically effective amount of a composition of claim 9.

16. A method for inhibiting farnesylation of Ras protein in said mammal which comprises administering to a mammal in need thereof a therapeutically effective amount of a composition of claim 10.

17. A method for inhibiting farnesylation of Ras protein in said mammal which comprises administering to a mammal in need thereof a therapeutically effective amount of a composition of claim 11.

18. A method for inhibiting farnesylation of Ras protein in said mammal which comprises administering to a mammal in need thereof a therapeutically effective amount of a composition of claim 12.

19. A method for inhibiting farnesylation of Ras protein in said mammal which comprises administering of a mammal in need thereof a therapeutically effective amount of a composition of claim 13.

20. A method for treating cancer, caused by activating mutations in the Ras gene, in said mammal which comprises administering to a mammal in need thereof a therapeutically effective amount of a composition of claim 8.

21. A method for treating cancer, caused by activating mutations in the Ras gene, in said mammal which comprises administering to a mammal in need thereof a therapeutically effective amount of a composition of claim 9.

22. A method for treating cancer, caused by activating mutations in the Ras gene, in said mammal which comprises administering to a mammal in need thereof a therapeutically effective amount of a composition of claim 10.

23. A method for treating cancer, caused by activating mutations in the Ras gene, in said mammal which comprises administering to a mammal in need thereof a therapeutically effective amount of a composition of claim 11.

24. A method for treating cancer, caused by activating mutations in the Ras gene, in said mammal which comprises administering to a mammal in need thereof a therapeutically effective amount of a composition of claim 12.

25. A method for treating cancer, caused by activating mutations in the Ras gene, in said mammal which comprises administering to a mammal in need thereof a therapeutically effective amount of a composition of claim 13.

* * * * *

UNITED STATES PATENT AND TRADEMARK OFFICE
CERTIFICATE OF CORRECTION

PATENT NO. : 5,468,733

DATED : November 21, 1995

INVENTOR(S) : S. Jane de Solms, Elizabeth A. Giuliani and Samuel L. Graham

It is certified that error appears in the above-identified patent and that said Letters Patent is hereby corrected as shown below:

At Column 22, Claim 2, line 38, should read as follows:

such as allyl, cyclohexyl, phenyl or saturated chains of.

At Column 24, Claim 10 and Claim 13 should read as follows:

10. A pharmaceutical composition comprising a pharmaceutical carrier, and dispersed therein, a therapeutically effective amount of a compound of claim 3.

13. A pharmaceutical composition comprising or a pharmaceutical carrier, and dispersed therein, a therapeutically effective amount of a compound of claim 7.

At Column 24, Claim 14, Claim 15 and Claim 16 should read as follows:

14. A method for inhibiting farnesylation of Ras protein in a mammal which comprises administering to said mammal in need thereof a therapeutically effective amount of a composition of claim 8.

15. A method for inhibiting farnesylation of Ras protein in a mammal which comprises administering to said mammal in need thereof a therapeutically effective amount of a composition of claim 9.

16. A method for inhibiting farnesylation of Ras protein in a mammal which comprises administering to said mammal in need thereof a therapeutically effective amount of a composition of claim 10.

At Column 25, Claim 17, Claim 18 and Claim 19 should read as follows:

17. A method for inhibiting farnesylation of Ras protein in a mammal which comprises administering to said mammal in need thereof a therapeutically effective amount of a composition of claim 11.

18. A method for inhibiting farnesylation of Ras protein in a mammal which comprises administering to said mammal in need thereof a therapeutically effective amount of a composition of claim 12.

19. A method for inhibiting farnesylation of Ras protein in a mammal which comprises administering to said mammal in need thereof a therapeutically effective amount of a composition of claim 13.

UNITED STATES PATENT AND TRADEMARK OFFICE
CERTIFICATE OF CORRECTION

PATENT NO. : 5,468,733

DATED : November 21, 1995

INVENTOR(S) : S. Jane de Solms, Elizabeth A. Giuliani and Samuel L. Graham

It is certified that error appears in the above-indentified patent and that said Letters Patent is hereby corrected as shown below:

At Column 25, Claim 20 and Claim 21 should read as follows:

20. A method for treating cancer, caused by activating mutations in the Ras gene, in a mammal which comprises administering to said mammal in need thereof a therapeutically effective amount of a composition of claim 8.

21. A method for treating cancer, caused by activating mutations in the Ras gene, in a mammal which comprises administering to said mammal in need thereof a therapeutically effective amount of a composition of claim 9.

At Column 26, Claim 22, Claim 23, Claim 24 and Claim 25 should read as follows:

22. A method for treating cancer, caused by activating mutations in the Ras gene, in a mammal which comprises administering to said mammal in need thereof a therapeutically effective amount of a composition of claim 10.

23. A method for treating cancer, caused by activating mutations in the Ras gene, in a mammal which comprises administering to said mammal in need thereof a therapeutically effective amount of a composition of claim 11.

UNITED STATES PATENT AND TRADEMARK OFFICE
CERTIFICATE OF CORRECTION

PATENT NO. : 5,468,733

DATED : November 21, 1995

INVENTOR(S) : S. Jane de Solms, Elizabeth A. Giuliani and Samuel L. Graham

It is certified that error appears in the above-indentified patent and that said Letters Patent is hereby corrected as shown below:

24. A method for treating cancer, caused by activating mutations in the Ras gene, in a mammal which comprises administering to said mammal in need thereof a therapeutically effective amount of a composition of claim 12.

25. A method for treating cancer, caused by activating mutations in the Ras gene, in a mammal which comprises administering to said mammal in need thereof a therapeutically effective amount of a composition of claim 13.

Signed and Sealed this

Third Day of September, 1996

Attest:

BRUCE LEHMAN

*Attesting Officer*    *Commissioner of Patents and Trademarks*